United States Patent
Fatemi (10) Patent No.: US 11,406,450 B2
(45) Date of Patent: Aug. 9, 2022

(54) DEVICE FOR IRRADIATING THE SKIN

(71) Applicant: Afschin Fatemi, Duesseldorf (DE)

(72) Inventor: Afschin Fatemi, Duesseldorf (DE)

(*) Notice: Subject to any disclaimer, the term of this patent is extended or adjusted under 35 U.S.C. 154(b) by 0 days.

(21) Appl. No.: 16/075,423

(22) PCT Filed: Feb. 17, 2017

(86) PCT No.: PCT/EP2017/053589
§ 371 (c)(1),
(2) Date: Aug. 3, 2018

(87) PCT Pub. No.: WO2017/140829
PCT Pub. Date: Aug. 24, 2017

(65) Prior Publication Data
US 2019/0038353 A1    Feb. 7, 2019

(30) Foreign Application Priority Data
Feb. 18, 2016   (EP) ..................... 16156270

(51) Int. Cl.
*A61B 18/20* (2006.01)
*A61N 5/06* (2006.01)
*A61B 18/00* (2006.01)

(52) U.S. Cl.
CPC .......... *A61B 18/203* (2013.01); *A61N 5/0616* (2013.01); *A61B 2018/0047* (2013.01); *A61B 2018/2035* (2013.01)

(58) Field of Classification Search
CPC .......... A61B 18/203; A61B 2018/0047; A61B 2018/202; A61B 2018/2035;
(Continued)

(56) References Cited

U.S. PATENT DOCUMENTS 4,205,902 A * 6/1980 Shafer ................... G02B 27/09
                                                              359/366
5,468,238 A * 11/1995 Mersch ................. A61B 18/20
                                                              600/108
(Continued)

FOREIGN PATENT DOCUMENTS

EP         1285680 A1    2/2003
JP      2000-316998 A    11/2000
(Continued)

OTHER PUBLICATIONS

PCT/EP2017/053589 International Search Report dated May 23, 2017.
JP2018-562700 Office Action dated Sep. 29, 2020.

*Primary Examiner* — Carl H Layno
*Assistant Examiner* — Jane C Kalinock
(74) *Attorney, Agent, or Firm* — Wagenknecht IP Law Group PC (57) ABSTRACT

A device and method for irradiating a target structure with laser radiation. The device has at least one laser light source and at least one optical element, by means of which the laser radiation is guided through a light outlet opening and focused at a focal point outside the light outlet. The optical element includes an arrangement of a convex mirror inside a hollow mirror, the mirrors being arranged such that laser radiation emitted from the laser light source enters the hollow mirror at least partially through an opening, and the laser radiation that passes through the opening hits the convex mirror, is deflected from the convex mirror to the hollow mirror, and passes through the light outlet opening from the hollow mirror.

19 Claims, 2 Drawing Sheets

(58) Field of Classification Search
CPC ........... A61B 2018/20553; A61B 2018/20359; A61B 2018/20554; A61N 5/0616
USPC .......................................................... 606/9
See application file for complete search history.

(56) References Cited

U.S. PATENT DOCUMENTS

| | | | | |
|---|---|---|---|---|
| 5,546,214 | A * | 8/1996 | Black | A61B 18/203 219/121.74 |
| 5,569,916 | A * | 10/1996 | Tomie | G01N 23/2273 250/287 |
| 5,786,924 | A | 7/1998 | Black et al. | |
| 5,995,265 | A * | 11/1999 | Black | G02B 26/0816 359/201.1 |
| 7,066,929 | B1 * | 6/2006 | Azar | A61B 18/203 606/10 |
| 2003/0036680 | A1 * | 2/2003 | Black | A61B 5/01 600/108 |
| 2007/0239147 | A1 | 10/2007 | Manstein et al. | |
| 2009/0059994 | A1 * | 3/2009 | Nemes | A61B 18/203 372/101 |
| 2010/0168824 | A1 * | 7/2010 | Toriser | A61N 5/06 607/90 |
| 2011/0137303 | A1 * | 6/2011 | Dolleris | A61N 5/0616 606/17 |
| 2011/0313408 | A1 | 12/2011 | Tankovich et al. | |
| 2013/0338654 | A1 * | 12/2013 | Wang | A61B 18/22 606/13 |
| 2014/0207053 | A1 * | 7/2014 | Morfill | A61L 2/0011 604/24 |
| 2015/0230863 | A1 | 8/2015 | Youngquist et al. | |

FOREIGN PATENT DOCUMENTS

| | | |
|---|---|---|
| JP | 2005-500108 A | 1/2005 |
| JP | 2005-218798 A | 8/2005 |
| JP | 2010-185664 A | 8/2010 |
| WO | 2013/156421 A1 | 10/2013 |
| WO | 2015/051999 A1 | 4/2015 |

* cited by examiner

DEVICE FOR IRRADIATING THE SKIN

CROSS REFERENCE TO RELATED APPLICATIONS

This application is a US national phase application under 35 USC § 371 of International patent application no. PCT/EP2017/053589, filed Feb. 17, 2017, which itself claims priority to European application 16156270.7, filed Feb. 18, 2016. Each of the applications referred to in this paragraph are herein incorporated by reference in their entireties.

TECHNICAL FIELD

The invention relates to a device and a method for irradiating a target structure with laser radiation and to a suitable use of a focal spot produced by the laser radiation. In this case the device has at least one laser light source and at least one light guiding means, which are configured in such a way that laser radiation enters the target structure via different beam paths, wherein an energy input resulting from the irradiation causes a change in the characteristics of the target structure at least in some regions.

BACKGROUND OF THE INVENTION

The beams emitted by a laser are characterised in particular by their high intensity, the very narrow frequency range of the radiation and the accompanying target-specific selectivity, a sharp focusing of the beam as well as the large coherence length. In addition to many known applications in the technical field, lasers are also frequently used in medical technology. Thus, for example in dermatology, incisions and sclerotherapy are carried out with the aid of laser beams. Likewise blood vessels can be coagulated by lasers of a specific wavelength, and pigmented spots can be removed or selectively destroyed with the aid of ablating or so-called peeling lasers. Furthermore, subcutaneous pigments are destroyed and thus removed with the aid of an ultrashort-pulse laser source, without causing lasting damage to the surface of the skin, or hair roots are permanently destroyed by epilation with the aid of long-pulse lasers. Furthermore, lasers are used in some instances for targeted treatment of inflammatory skin diseases, such as for instance psoriasis, or superficial irregularities of the skin, such as nodules or wrinkles, are smoothed (resurfacing) for cosmetic improvement of the complexion. According to a further application in dermatology, lasers are used in order to selectively heat dermal sections and thus to promote collagen formation and to tighten the skin in this area (subsurfacing).

Depending upon the type of laser used, different interactions occur between the skin or the tissue and the light emitted by the laser. The type of interaction depends, on the one hand, upon the optical characteristics of the skin or of the tissue, in particular the dispersion and absorption coefficients as well as the density and, on the other hand, upon the physical parameters of the laser light, in particular the wavelength, the energy density, the repetition rate, the irradiation duration as well as the spot size.

The laser/tissue interactions are divided into different mechanisms. These include the photothermal, photomechanical or photoacoustic and the photochemical interaction. Furthermore, the phenomenon of light-induced ablation, so-called photoablation, is also used in some instances. Under these effects the most quantifiable and generally observed reaction is the photothermal effect which is achieved by the introduction of high energies and the evaporation of water in the tissue which is caused thereby. Depending upon the condition of the irradiated medium and the corresponding structure as well as the irradiation parameters, the different effects occur to different extents, it being assumed that the absorbed energy and the irradiation time for the most part influence the tissue effects. The corresponding interactions are described in detail in "C. Raulin, S. Kasei (Hrsg.), Lasertherapie der Haut, Springer-Verlag Berlin, Heidelberg 2013".

In this connection a laser for treatment of the skin is described in US 2011/0313408 A1. In the described technical solution it is significant that for the irradiation a first laser beam with a long pulse duration and a second laser beam with a short pulse duration are used simultaneously with a cooling element for cooling a surface region of the skin. A volume of skin tissue below the cooled surface region is heated by the first laser beam in order to modify the skin tissue still below the skin tissue damage threshold. The second laser beam is divided into a plurality of separate laser beams with the aid of separate optical fibres and is guided via separate paths through the skin tissue into the preheated skin tissue, in order to cause mechanical damage here in specifically selected small volumes.

Furthermore, a system for treating dermatological diseases which is based on the thermal damage of a target structure is known from US 2007/0239147 A1. In this case a beam is directed specifically onto a target point on the surface of the skin, in order to damage the target structure in the tissue below this target position. In particular, light guiding means are provided, by which a second beam of light is guided onto the same target position in order to damage another volume of tissue thermally below the target site.

Furthermore, U.S. Pat. No. 7,066,929 B1 discloses a selective photothermolysis, by which subcutaneous tissue is destroyed by the use of a plurality of beams of narrow-band, electromagnetic waves. Since each of the beams does not have sufficient energy in order to heat the tissue to the required temperature and to destroy the tissue by overheating, the individual beams are overlapped at the target point in such a way that sufficient heat is generated in order to destroy the target tissue. According to the described technical solution a beam guiding device is provided for this purpose which guides the individual light beams in such a way that each of the beams exits at a different angle as it leaves the irradiation device. With the aid of a suitable control of the laser the different individual beams are finally focused in one point.

Furthermore, WO 2013/156421 A1 likewise describes a device for treatment of skin and/or tissue layers with the aid of laser light. A significant feature of the described device is that a plurality of laser light sources is used in order simultaneously or alternately to irradiate a target structure from different directions. The laser light source and/or suitable light guiding means are arranged in such a way that the laser light is focused at certain points on different paths into the layer of skin or tissue to be treated and in the region of the target structure.

One problem which often occurs with the known and currently used technical solutions for treatment of the skin is that damage is caused to the skin area on which the laser radiation impinges, in order to penetrate from there further into the skin or the subcutaneous tissue. Such damage is regularly undesirable and in some instances can lead to significant complications. Furthermore, in many cases it constitutes a considerable problem to destroy larger target structures, in particular those located subcutaneously at a comparatively great depth, in a targeted manner, without damage occurring to adjoining areas of tissue, glands or other parts of the skin or of the tissue. This is attributable in particular to the fact that with the known technical solutions it is not possible to a sufficient extent to achieve a sufficient and nevertheless locally delimited energy input into an extensive target structure within the skin or the subcutaneous tissue.

BRIEF SUMMARY OF THE INVENTION

Starting from the technical solutions known from the prior art as well as the previously described problems, the object of the invention is to make further developments to a device for treatment of the skin of a person or of an animal by means of a laser in such a way that the required energy input takes place at least almost exclusively into the target structure to be damaged. In this case in particular damage to the epidermis of the skin on which laser radiation occurs should be avoided and overall the energy input into the skin or the tissue should be reduced to the respectively required minimum amount. Furthermore, the described system should be capable of being integrated in a comparatively simple manner into a compact apparatus, and should facilitate economically viable use in daily operation. Furthermore, the system to be provided should be designed in such a way that a more flexible use, in particular carrying out a plurality of different treatments of the skin and of the tissue located below it, is possible.

In one aspect of the invention a device for irradiating a target structure located within human or animal skin or tissue is provided. The device includes at least one laser light source and at least one optical element, by means of which the laser radiation is guided through a light outlet opening and is focused in a focal point outside the light outlet opening, where at least one adjustment element is used to adjust the distance between the surface of the skin and the focal point positioned in the region of the target structure. The optical element has an arrangement of a convex mirror inside a hollow mirror. The mirrors are arranged such that laser radiation emitted from the laser light source enters the hollow mirror at least partially through an opening, and the laser radiation that passes through the opening hits the convex mirror, is deflected from the convex mirror to the hollow mirror, and passes through the light outlet from the hollow mirror.

In some embodiments, the adjustment element has a spacer, which can be placed onto the surface of the skin in such a way that a distance between the light outlet opening and the skin is adjustable. In further embodiments, the spacer has an actuator by means of which the spacer is at least partially movable in such a way that at least two different distances between the light outlet opening and the surface of the skin can be set.

In some embodiments, the adjustment element has at least one moving means, by which at least one component of the optical element is movable in such a way that the distance between the light outlet opening and the focal point is adjusted on the basis of the movement.

In some embodiments, at least one cooling element is provided, by which a surface of the skin, in particular a surface of the stratum corneum, can be cooled.

In some embodiments a control unit is provided, which at least intermittently transmits a control signal to the laser light source, the optical element and/or the adjustment element. In some embodiments, characteristics of at least one layer of skin and/or of a tissue type are stored in the control unit or a data memory coupled to the control unit. In some embodiments, at least one optical characteristic, in particular a value for an index of refraction and/or for an absorption capacity of at least one area of skin and/or tissue, is stored in the control unit or a data memory coupled to the control unit.

In some embodiments, the laser light source has an He—Ne laser, a Nd-YAG laser and/or a Er-YAG laser.

In some embodiments, the laser light source, the optical element and the adjustment element are surrounded by a single-part or multi-part housing, in which the light outlet opening is located and on which a handle for manual guiding is fastened.

In some embodiments, between the laser light source and the convex mirror a diffuser optic is arranged, by which an intensity distribution of the laser light radiation is changed in such a way that the laser light radiation has a lower intensity in a centre of the beam than in the edge region.

In a related aspect of the invention a method for generating a focal spot or focal point for targeted change of at least one material characteristic of a component in a target structure, where laser radiation is generated with at least one laser light source and is guided by at least one optical element at least partially through a light outlet opening and is focused in a focal point outside the light outlet opening, where with the aid of at least one adjustment element a distance between a component surface and the focal spot or focal point positioned in the region of the target structure can be adjusted. The laser radiation which is emitted from the laser light source, comes at least partially from a rear side lying opposite a mirror surface passes through an opening in a hollow mirror, and the laser radiation that passes through the opening is guided to a convex mirror, is deflected from the convex mirror onto the mirror surface of the hollow mirror and, coming from the hollow mirror, is guided through the light outlet opening to the focal spot or focal point.

In another related aspect of the invention, an arrangement for irradiating a target structure which is located within human or animal skin or tissue is provided, which includes at least two devices provided herein.

In yet another related aspect of the invention, use of a laser beam generated by a device according to the device or method, for the treatment of acne, skin impurities, haemangiomas, cellulitis, hyperhidrosis, skin cancer, wrinkles, varicosis, disc prolapse and/or fat is provided

BRIEF DESCRIPTION OF THE DRAWINGS

The invention is explained in greater detail below, without limitation of the general concept of the invention, on the basis of an embodiment with reference to the drawings.

DETAILED DESCRIPTION OF THE INVENTION

The invention relates to a device for irradiating a target structure which is located within human or animal skin or tissue, in particular subcutaneous tissue. The device has at least one laser light source and at least one optical element by means of which the laser radiation is guided through a light outlet and focused in a focal point outside the light outlet. The invention also relates to at least one adjustment element used to adjust the distance between the surface of the skin and the focal point positioned in the region of the target structure. The device is further developed in that the optical element has an arrangement of a convex mirror inside a hollow mirror, the mirrors being arranged such that laser radiation emitted from the laser light source enters the hollow mirror at least partially through an opening, and the laser radiation that passes through the opening hits the convex mirror, is deflected from the convex mirror to the hollow mirror, and passes through the light outlet from the hollow mirror.

The arrangement a convex mirror inside a hollow mirror corresponds substantially to the configuration of a Schwarzschild objective, where, however, the beam path of the laser beam extends from the laser light source to the outlet opening and further to the focal point of the hollow mirror. Thus the optical element has two centrally arranged mirrors or reflector elements which lie opposite one another. The main mirror is designed as a concave hollow mirror, the mirror surface of which is oriented in the direction of the light outlet opening. The significantly smaller, convex mirror, also referred to as a collecting mirror or collecting reflector, is located as a convex mirror in a position close to the light outlet opening, wherein its mirror surface faces the main mirror.

Thus the laser light emitted by the laser light source falls through an opening in the hollow mirror onto the small collecting mirror, is deflected thereby in the radial or spherical or hemispherical direction onto the hollow mirror, which finally directs the laser radiation through the outlet opening into the environment of the device.

In this connection it is conceivable that the hollow mirror is configured either as a parabolic mirror or as a spherical hollow mirror. In this case a parabolic mirror is characterised in that all light beams which impinge on the mirror parallel to the optical axis are focused exactly in the focal point. On the other hand, a spherical hollow mirror which has the shape of a spherical sector is comparatively simple and therefore cost-effective to produce. In principle it is advantageous to configure the hollow mirror integrally. In general, however, a multi-part, in particular two-part configuration is also conceivable, wherein in any case an opening should preferably be provided centrally, through which the radiation coming from the laser light source can pass through, in order to be able to impinge on the convex mirror.

The center point of the convex mirror, in particular the location closest to the laser light source, is preferably located on the optical axis of the laser beam emitted by the laser light source.

In order to position the focal point inside the target structure, the laser light source with the optical element must be moved a corresponding distance to the target structure. The target structure is often not located directly on the surface of the skin, but is located below the surface of the skin, for instance in the subcutaneous tissue. The penetration depth of the laser radiation provided for the treatment and here, in particular, the distance of the focal point from the surface of the skin must be set according to the position of the target structure. In this connection the penetration depth of the radiation is routinely understood to be the depth of the focal point inside the body of the patient, that is to say the distance of the focal point from the surface of the skin.

If the target structure is not located directly on the surface of the skin this has the effect, in relation to the laser radiation impinging on the surface of the skin, that the contact area on the surface of the skin has a circular or elliptical shape, whilst the radiation is focused in the focal point which is then located below the surface of the skin in the target structure. Thus the energy input on the surface of the skin which is not to be treated and for which lasting damage should be prevented, is minimised. On the other hand, the maximum energy input is achieved within the target structure, namely in the focal point. In this connection it is pointed out that according to the invention the radiation is regularly not focused exactly in a focal point but in fact is focused in a focal area or focal volume, wherein in this area the intensity of the incident laser radiation is at a maximum.

Thus it is significant for the positioning of the focal point or the focal area in the target structure that the adjustment element provided according to the invention is used for targeted adjustment of the distance between the surface of the skin and the focal point positioned in the region of the target structure. In the simplest embodiment this adjustment is achieved in that the laser light source with the optical element and the outlet opening, which are preferably arranged in and/or on an apparatus housing, is moved manually or by a robot arm into a position so that the focal point or the focal area comes to lie within the target structure. In order to be able to adjust the required distance from the surface of the skin an adjustment element is provided, by which the distance between a surface of the skin and the focal point positioned in the region of the target structure can be adjusted in a targeted manner.

In a specific further embodiment of the invention the adjustment element is designed as a spacer which adjusts the respectively required distance between the surface of the skin and the light outlet opening. For this purpose it is significant that due to a change of the distance between the light outlet opening and the surface of the skin, at least with unchanged optical settings, the distance between the surface of the skin and the focal point is changed simultaneously. In this way by the choice of the suitable spacer the penetration depth of the focal point of the radiation within the skin or the tissue lying below the skin can be changed.

In principle it is conceivable in this connection to provide a plurality of spacers of different sizes, in particular of different lengths, which are for example fastened replaceably on a housing of the device configured according to the invention.

In a further embodiment of the invention it is provided that the spacer has an actuator by means of which the spacer is at least partially movable in such a way that at least two different distances between the outlet opening and the skin can be set. Such an actuator can be configured for example in the form of a lever or adjusting wheel with movable elements coupled thereto, so that a length of the spacer can be adjusted to the required distance between the light outlet opening and the surface of the skin. Alternatively or in addition it is conceivable that the actuator preferably has electrically driven elements, for example an electric motor, which if required can be combined with a gear mechanism, by means of which the spacer can be extended to the corresponding length, or by which the required distance between the light outlet opening and the surface of the skin can be set.

A further embodiment of the invention provides that the adjustment element has at least one moving means, by which at least one component of the optical element is movable in such a way that the distance between the outlet opening and the focal point is adjusted on the basis of the movement. This embodiment offers the advantage that the device can be placed onto the surface of the skin at a constant distance and the penetration depth of the focal point within the skin is adjustable by a displacement of at least one component of the optical element. The moving means is preferably connected mechanically to at least one of the two mirrors of the optical element and can move at least one of these mirrors in such a way that the penetration depth of the laser radiation can be adjusted to the required value. Self-evidently the use of pneumatically or electromagnetically driven moving means is also conceivable.

Furthermore, in a special embodiment at least one cooling element is provided, by which a surface of the skin, in particular a surface of the stratum corneum, can be cooled. The use of such a cooling element, by which the surface of the skin on which the laser radiation impinges is cooled in a targeted manner, offers the advantage that heating of the skin by the incident laser radiation can be counteracted. In this connection it is advantageously conceivable that the cooling of the skin takes place in a regulated manner, wherein the respective power of the laser light emitted by the laser light source is taken into consideration for the regulation of the cooling.

Furthermore, a control unit is preferably provided, which at least intermittently transmits a control signal to the laser light source and/or the adjustment element. With such a control unit it is possible, on the one hand, to change the intensity of the laser radiation emitted by the laser light source and, on the other hand, to change the penetration depth of the laser radiation into the skin or into the subcutaneous tissue in a targeted manner and thus to adapt to the patient-specific requirements or the planned treatment.

Furthermore a data memory is preferably provided which is located inside the control unit or is at least connected thereto, and in which characteristics of the tissue to be treated or to be irradiated are stored. In particular, optical characteristics of different areas of skin and/or tissue or corresponding skin and/or tissue types are stored here, so that the laser light source and/or the optical element can be adjusted with the aid of a control signal generated by the control unit in such a way that a targeted treatment of the target structure takes place without lasting damage to the surrounding tissue which is not to be treated.

Values for specific optical characteristics, such as for example the index of refraction and/or the absorption capacity of various skin or tissue types, are preferably stored in the data memory. In an advantageous manner the required values can be selected by the user before treatment and automatically form the basis for the control of the laser light source and/or of the optical element.

In a specific further embodiment of the invention the laser light source is a light source which can be regulated with regard to the intensity and/or the emitted light wavelength. The laser light source preferably has an He—Ne laser, a Nd-YAG laser and/or a Er-YAG laser.

According to a particular embodiment of the invention it is provided that at least two, preferably an even larger number of laser sources is used in order, on the one hand, to enlarge the area to be treated and/or, on the other hand, to provide different potential routes by means of which the laser light radiation reaches the area to be treated through the skin and the body of the patient. In this connection it is advantageous if an optical element configured according to the invention with the two previously described mirrors is associated with the corresponding laser light sources. Furthermore, it is advantageous if at least one of the laser light sources and/or the respectively associated optical element is movable. The movement takes place for example with a suitable adjustment motor which is controlled by the control unit as a function of the type and progress of the treatment. In a quite particular further embodiment, a plurality of laser light sources having optical elements fastened thereto are provided, arranged on a circle or segment of a circle and fastened to a corresponding frame. In this case the frame and/or the assembly fastened thereon, at least consisting of the laser light source and the optical element, can be designed to be movable.

The previously described components of a device configured according to the invention are preferably located in an apparatus housing which has at least one handle for manual guiding and actuation of the device. In the region of the handle at least one switching element is preferably provided, by which the laser light source can be switched on and/or required parameters can be input in particular as guide or target values. According to a specific further embodiment of the invention, settings of the adjustment element and/or of the optical element can also be changed in a targeted manner by this switching element or a further switching element, so that a distance between the light outlet opening and the focal point can be adjusted to the required value.

Furthermore, the apparatus housing has at least one indicator unit, in particular a display, for displaying selectable parameters stored in the data memories, actual values occurring during the use of the device and/or preset or input target values.

In addition to a device, the invention also relates to a method for generating a focal spot or focal point for targeted change of at least one material characteristic of a component in a target structure. During implementation of the method according to the invention the sequence of method steps set out below is produced:

generating a laser beam with a laser light source and guiding the laser beam, with the aid of an optical element to a light outlet opening, so that the beam is focused outside the light outlet opening in the focal point or focal spot, and setting a distance between a component surface and the focal spot or focal point positioned in the region of the target structure by means of an adjustment element.

The method according to the invention is characterised in that the laser radiation which is emitted from the laser light source and comes at least partially from a rear side lying opposite a mirror surface passes through an opening in the hollow mirror, and the laser radiation that passes through the opening is guided to a convex mirror, is deflected from the convex mirror onto the mirror surface of the hollow mirror and, coming from the hollow mirror, is guided through the outlet opening to the focal spot.

With the aid of the previously described device as well as the method, it is possible in a preferred manner to make changes in the characteristics of a material in a target structure, in particular in a target structure which is located in the skin and/or in subcutaneous tissue of a person or of an animal. In this connection the device according to the invention and in particular the laser radiation generated by this device in the region of the focal point or focal spot can be used for the treatment of acne, skin impurities, haemangiomas, cellulitis, hyperhidrosis, skin cancer, wrinkles, varicosis, disc prolapse and/or fat.

Figure 1:
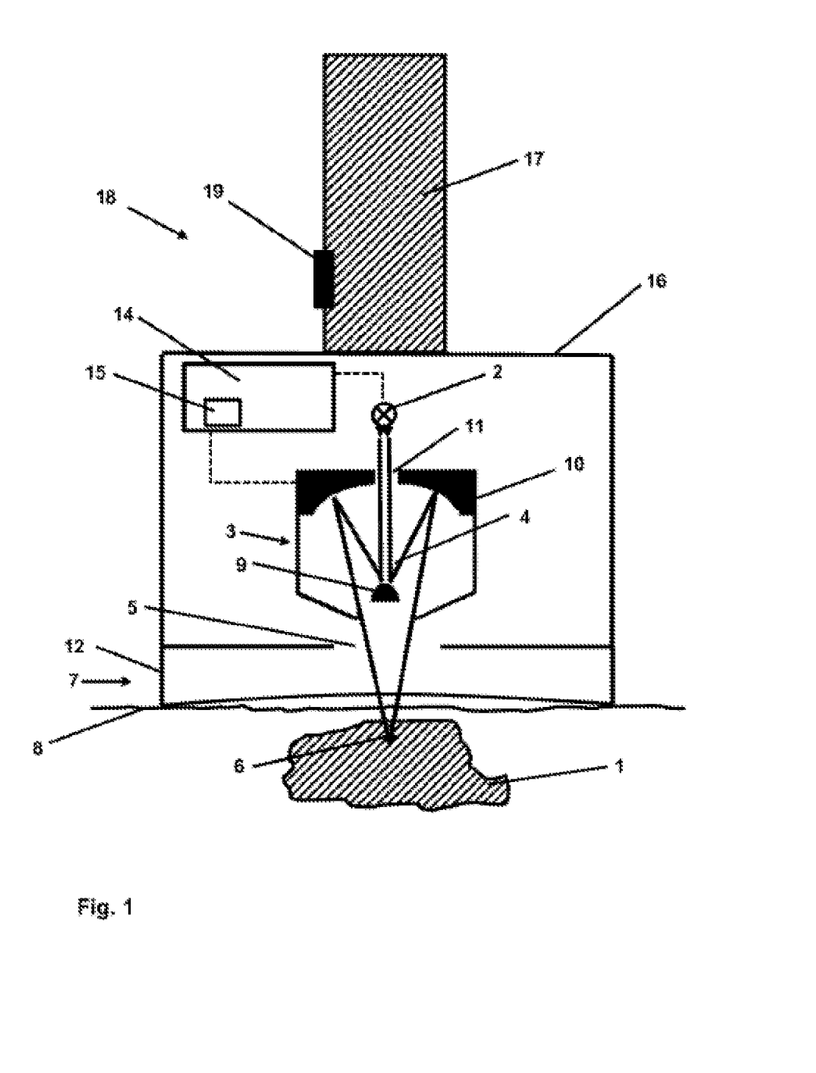
FIG. 1 shows an apparatus which can be guided manually with a device configured according to the invention for generating a laser beam directed into a target structure.

Referring now to FIG. 1, an exemplary device according to the invention is shown, which is designed as a manually guided apparatus 18 for carrying out dermatological treatments by means of laser light 4. The irradiating apparatus 18 can be operated and guided manually and for the treatment is held above the area to be irradiated with the target structure 1. The illustrated irradiating apparatus 18 essentially includes a housing body 16, in which a laser light source 2, an optical element 3 and a light outlet opening 5 are arranged, as well as an adjustment element 7 and a handle 17 for guiding the device which are fastened to the housing 16. In the region of the handle 17 a manual switch is provided as a switching element 19 by means of which the laser light source 2 can be switched on and off.

With the illustrated manual irradiation apparatus 18 it is possible to carry out a treatment of diseased skin or subcutaneous tissue in a simple manner. A laser light source 2 for generating laser radiation 4 is provided inside the apparatus housing 16. The laser beam 4 is guided through an opening 11 in a hollow mirror 10, coming from the rear side thereof, onto a convex mirror 9 which is arranged in the interior of the hollow mirror 10 on the optical axis of the laser radiation 4. From this convex mirror 9 the laser radiation 4 is directed onto the mirror surface of the hollow mirror 10 and from there through the light outlet opening 5 provided in the wall of the housing 16, so that the radiation 4 is focused in the region of the focal point or focal spot 6.

A spacer 12 fastened replaceably to the housing is provided as an adjustment element 7 which is placed onto the surface of the patient's skin 8 above the target structure 1 and defines a fixed distance between the light outlet opening 5 and the surface of the skin 8, so that the distance between the surface of the skin 8 and the focal point or focal spot 6 is defined and is known to the user. In this case different spacers 12 are advantageously provided which, as a function of the requirements, in particular as a function of the required depth of penetration into the skin or into the tissue located below it, can be fastened alternatively on the housing 16 of the irradiating apparatus 18 and in each case set a predetermined distance between the light outlet opening 5 and the surface of the skin 8. Likewise it is conceivable to provide an adjustment element 7 which is fastened to the housing 16 of the irradiating apparatus 18 and has moveable components, so that the distance between the light outlet opening 5 and the surface of the skin 8 can be set in an appropriate and targeted manner. An adjustment can be made manually, for example with the aid of a screw mechanism, or with the aid of a driving element, such as for instance an electric motor.

The maximum external diameter of the manual irradiation apparatus 18 in the region of the housing body 16 is approximately 6 cm. In a particular design this diameter is approximately 3.5 to 5 cm.

In the controller 14, in which control signals for operation of the laser light source 2 are generated, optical characteristics of the tissue to be irradiated and the skin are stored in a data memory 15. Before the start of treatment the user locates a treatment region within the skin or the subcutaneous tissue and defines a suitable three-dimensional target structure 1 which is to be irradiated. Furthermore, for the irradiation the defined radiation parameters of the laser radiation 4 as well as the optical characteristics of the irradiated regions stored in the controller 14, inter alia the surface of the skin 8, on the one hand, and the target structure 8, on the other hand, are taken into account. In this way it is ensured that during the treatment in the skin or in the subcutaneous tissue at least one three-dimensional focal spot 6 is generated, in which the required changes in the characteristics are effected.

Figure 2:
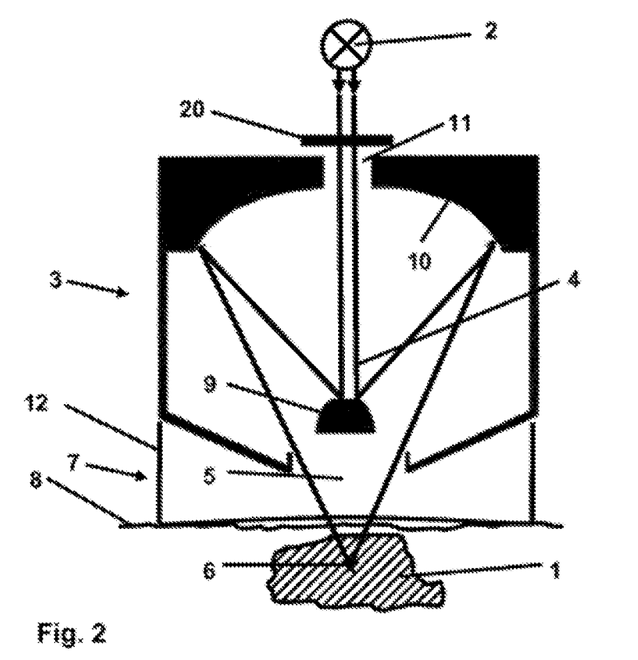
FIG. 2 shows a schematic representation of a laser light source having an optical element which enables beam guidance according to the invention.

Turning to FIG. 2, a schematic representation of a laser light source 2 having an optical element 3 is shown, which enables beam guidance according to the invention. With the aid of the illustrated apparatus a focal point or a focal spot 6 extending three-dimensionally is generated within the target structure 1. In this case it is significant that the radiation 4 emitted by the at least one laser light source 2 is directed onto the area to be treated, in particular into the target structure 1, with the aid of a hollow mirror 10 and a convex mirror 9 arranged centrally in the hollow mirror, which are arranged as in a Schwarzschild objective.

The arrangement of hollow mirror 10 and convex mirror 9 used in this case for the optical elements is characterised in particular in that a beam of light 4, which has an inhomogeneous intensity distribution with higher intensity in the centre of the beam than at the edge of the beam, as is the case for example with light beams which are emitted by excimer lasers, and this is illustrated on a smaller scale. Excimer lasers emit coherent UV light beams of high intensity and are therefore frequently used in medicine.

The two mutually opposing, centrally arranged mirrors 9, 10 are very important for the arrangement according to the invention of the mirrors 9, 10 of the optical element 3. The main mirror is designed as a hollow mirror 10, the mirror surface of which is directed towards the light outlet opening 5 or towards the surface of the skin 8. The significantly smaller collecting mirror 9 is located as a convex mirror in the direction towards the light outlet opening 5, wherein its mirror surface is directed towards the main mirror 10.

The light beams 4 emitted by the laser light source 2 first of all enter into a diffuser optic 20, by which an intensity distribution of the light beam 4 before entry into the arrangement of the hollow mirror 10 and the convex mirror 9 is changed in such a way that the light beam 4 has a lower intensity in the center than in the edge regions. For this purpose the diffuser optic 20 can have for instance a biprism and a homogeniser. Next the light beams 4 are focused onto the defined target structure 1 with the aid of the convex collecting mirror 9 and the hollow mirror 10.

It is significant for the illustrated technical solution that the laser radiation 4 is focused in the region of the target structure 1, so that the radiation intensity in the region of a focal spot 6 located in the target structure 1 reaches a maximum and that, on the other hand, those regions of skin and tissue which should not be changed in a lasting manner are only exposed to a comparatively low radiated power or radiation dose. This is attributable to the special beam guidance, in which the radiation 4 is distributed, in particular in the region of the surface of the skin 8, onto a comparatively large circular ring area. Thus the laser radiation 4 can be accurately focused in the target structure 1.

In order in specific cases to provide an additional measure for protection of the skin on which at least a part of the laser radiation impinges intermittently, as a function of the selected treatment a cooling element is provided which cools the surface of the skin 8 and thus additionally protects it against unwanted damage due to the laser treatment.

Figure 3:
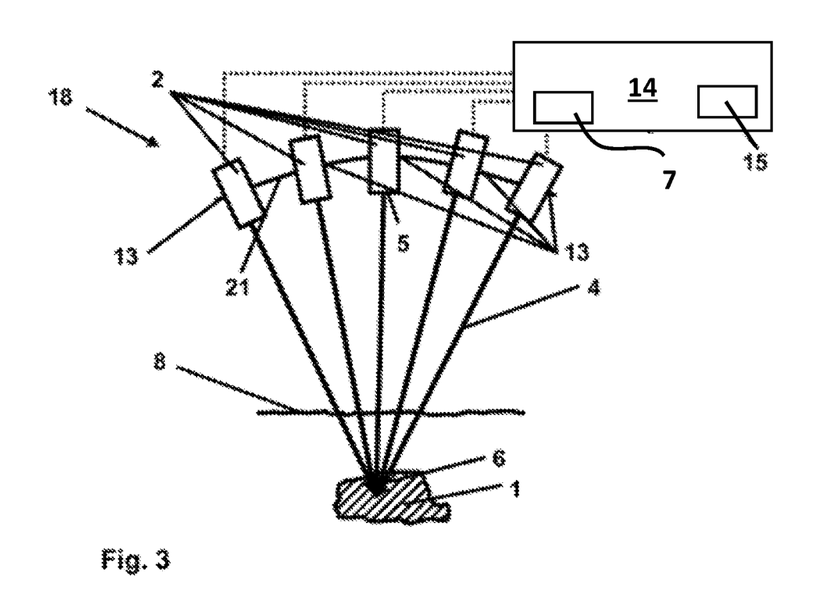
FIG. 3 shows an arrangement for carrying out a dermatological treatment with a plurality of assemblies comprising a laser light source and an optical element.

Moving to FIG. 3, a specific arrangement of assemblies are shown, which in each case include a laser light source 2 and an optical element 3 with two mirrors which are arranged as is known from a Schwarzschild. The laser light sources 2 with the optical elements 3 connected downstream thereof are fastened to an apparatus holder 21, where in each case moving means 13 are provided with adjustment motors which, on the basis of a control signal generated by a central controller 14, move the laser light sources 2 with the optical elements 3 as required. With the aid of such an arrangement of a plurality of light sources 2, which are arranged according to the exemplary embodiment illustrated in FIG. 3, it is possible, on the one hand, to carry out irradiation over a particularly large surface area in a treatment phase and, on the other hand, it is thus made possible to radiate laser light beams 4 into the body on different beam paths. Due to this measure the intensity of irradiation can be varied as required over a wide range during a treatment, and at the same time different regions of a target structure can be irradiated and/or the radiation load of the upper layers of the skin can be limited in a suitable manner without delays occurring in the treatment.

FIG. 3 shows a schematic representation of an arrangement with a plurality of movable assemblies in each case with a laser light source 2 and optical unit 3. As already explained in connection with FIGS. 1 and 2, the optical units 3 have a hollow mirror 10 and a convex collecting mirror 9, the mirror surfaces of which face one another and which enable beam guidance, as is known for instance from Schwarzschild objectives. On the basis of the data input by the user and/or parameters which are stored in a data memory 15 and can contain information about skin, tissue and beam characteristics, the control unit 14 which is provided generates control signals in order to adjust the laser light sources 2, the optical elements 3 and/or the moving means 13 in a suitable manner and to ensure successful treatment with minimum damage to the healthy tissue and the healthy skin. In this connection, by means of the central control unit 14 the required distance between the light outlet openings 5 and the surface of the skin 8 is also set. In order to effect a suitable adjustment, the control unit 14 together with corresponding suitable moving means 13 takes on the function of the adjustment means 7 for controlled movement of the apparatus holder 21, the laser light sources 2 and/or the optical element 3, in particular the mirrors 9, 10. Such an automated adjustment of different components and thus of the distance between the light outlet openings 5 and the surface of the skin 8 and thus also between the surface of the skin 8 and the target structure 1, in order thus to generate a focal point or focal spot within the target structure 1, preferably takes place with the aid of a stationary irradiating apparatus.

Likewise it is possible to miniaturise such an arrangement, so that there is space for the arrangement in an apparatus 18, which can be guided manually. It is significant in each case that with a corresponding arrangement, regardless of its overall size, at least two laser beams which pass through the patient's body in the direction of the target structure 1 at least in part on different paths or at different times are generated either concurrently, overlapping in time or staggered at intervals. If a corresponding arrangement is installed in a manually guided apparatus, it is advantageous if information as to whether the apparatus is located in the correct position relative to the target structure 1, in particular at the correct distance from the surface of the skin 8, is output to the handler, in particular by means of an external display or a display integrated in the handheld apparatus. The information is output in such a way that the user can recognise in a simple manner whether, and in which direction, the apparatus must be moved.

LIST OF REFERENCES 1 target structure
2 laser light source
3 optical element
4 laser light beam
5 light outlet opening
6 focal point/focal spot
7 adjustment element
8 surface of the skin
9 convex mirror
10 hollow mirror
11 opening in the hollow mirror
12 spacer
13 moving means
14 control unit
15 data memory
16 housing
17 handle
18 irradiating apparatus
19 switching element
20 diffuser element
21 apparatus holder

What is claimed is:

1. A device for irradiating a target structure located within human or animal skin or tissue, the device comprising:
at least one laser light source;
at least one optical light guide disposed adjacent the at least one laser light source, each of the at least one optical light guide comprising:
a hollow mirror having a concave mirror surface and an opening extending through the hollow mirror; and
a convex mirror facing the concave mirror surface of the hollow mirror;
at least one adjustment element for adjusting a distance between a surface of the skin and a focal point that is configured for targeting both structures on a surface of the skin and subcutaneous structures;
a light outlet opening adjacent the at least one optical light guide, such that at least a portion of the laser radiation emitted from the at least one laser light source passes through the opening extending through the hollow mirror, hits the convex mirror, is deflected from the convex mirror to the concave mirror surface of the hollow mirror, is deflected from the concave mirror surface directly towards the light outlet opening, and passes through the light outlet opening; and
a diffuser optic comprising a biprism and a homogenizer, wherein the diffuser optic is disposed between the at least one laser light source and the convex mirror, the diffuser optic being adapted to adjust an intensity distribution of the laser radiation from the at least one laser light source in such a way that the adjusted laser radiation has a lower intensity in a center of a beam of the laser radiation than in an edge region of the beam of the laser radiation.

2. The device according to claim 1, wherein the at least one adjustment element includes a spacer adapted to be placed onto the surface of the skin in such a way that a distance between the light outlet opening and the surface of the skin is adjustable.

3. The device according to claim 2, wherein the at least one adjustment element includes an actuator configured to move the spacer to at least two different distances between the light outlet opening and the surface of the skin.

4. The device according to claim 1, wherein the at least one adjustment element includes at least one moving means adapted to move at least one component of the optical light guide to adjust a distance between the light outlet opening and the focal point.

5. The device according to claim 1, further comprising a control unit configured to at least intermittently transmit a control signal to at least one of the at least one laser light source, the at least one optical light guide and the at least one adjustment element.

6. The device according to claim 5, wherein at least one of the characteristics of at least one layer of skin and of a tissue type associated with the target structure are stored in at least one of the control unit and a data memory electrically coupled to the control unit.

7. The device according to claim 5, wherein at least one of an optical characteristic, a value for an index of refraction and an absorption capacity of at least one area of skin and/or tissue associated with the target structure is stored in at least one of the control unit and a data memory electrically coupled to the control unit.

8. The device according to claim 1, wherein the at least one laser light source includes one of a He—Ne laser, a Nd-YAG laser and an Er-YAG laser.

9. The device according to claim 1, further comprising:
one of a single-part housing and a multi-part housing including the light outlet opening, wherein the at least one laser light source, the at least one optical light guide and the at least one adjustment element are contained within the one of the single-part and the multi-part housing; and
a handle coupled to the one of the single-part housing and the multi-part housing and adapted to manually guide the at least one adjustment element to adjust the distance between the surface of the skin and the focal point.

10. A method for generating a focal point for targeted change of at least one material characteristic of a component in a target structure comprising:
providing the device according to claim 1;
generating laser radiation from at least one laser light source;
receiving at least a portion of the laser radiation at a convex mirror of an optical light guide via an opening in a hollow mirror of the optical light guide;
deflecting the portion of the laser radiation from the convex mirror to a concave mirror surface of the hollow mirror;
deflecting the portion of the laser radiation from the concave mirror surface of the hollow mirror directly towards and through a light outlet opening to the focal point; and
adjusting a distance between a component surface and the focal point with respect to a region of the target structure.

11. The device according to claim 1, wherein the device is a component of a system comprising at least two devices.

12. The device according to claim 1, wherein the target structure is a subcutaneous structure.

13. The device of claim 1, wherein the light outlet opening is positioned within an angled terminal end of the optical light guide so that laser radiation that is not deflected directly at the light outlet opening is deflected in a direction of the concave mirror.

14. A system for irradiating a target structure located within human or animal skin or tissue comprising:
an apparatus holder; and
first and second assemblies coupled to the apparatus holder, each of the first and second assemblies comprising:
a laser light source;
an optical light guide disposed adjacent the laser light source, the optical light guide comprising:
a hollow mirror having a concave mirror surface and an opening extending through the hollow mirror; and
a convex mirror facing the concave mirror surface of the hollow mirror;
an adjustment element for adjusting a distance between a surface of the skin and a focal point that is configured for targeting both structures on a surface of the skin and subcutaneous structures;
a light outlet opening adjacent the optical light guide; and
a diffuser optic comprising a biprism and a homogenizer;
wherein at least a portion of the laser radiation emitted from the laser light source of the first assembly is guided along a first path that passes through the opening extending through the hollow mirror of the first assembly, hits the convex mirror of the first assembly, is deflected from the convex mirror of the first assembly to the concave mirror surface of the hollow mirror of the first assembly, is deflected from the concave mirror surface of the first assembly directly towards and through the light outlet opening of the first assembly;
wherein at least a portion of the laser radiation emitted from the laser light source of the second assembly is guided along a second path that passes through the opening extending through the hollow mirror of the second assembly, hits the convex mirror of the second assembly, is deflected from the convex mirror of the second assembly to the concave mirror surface of the hollow mirror of the second assembly, is deflected from the concave mirror surface of the second assembly directly towards and through the light outlet opening of the second assembly, the first path being different from the second path; and
wherein the laser radiation has a lower intensity in a center of a beam of the laser radiation than in an edge region of the beam of the laser radiation.

15. The system of claim 14, further comprising a control unit configured to at least intermittently transmit a control signal to at least one of the laser light source, the optical light guide and the adjustment element of the first and second assemblies.

16. The system of claim 15, wherein the control unit is configured to issue a first control signal to the adjustment element of the first assembly to adjust the distance between the surface of the skin and the focal point of the first assembly to position the focal point of the first assembly with respect to a first area of the target structure, and to issue a second control signal to the adjustment element of the second assembly to adjust the distance between the surface of the skin and the focal point of the second assembly to position the focal point of the second assembly with respect to a second area of the target structure, the first area of the target structure being different from the second area of the target structure.

17. A method for irradiating a target structure located within human or animal skin or tissue comprising:
simultaneously generating laser radiation from first and second laser light sources of first and second assemblies, respectively, the first and second assemblies being coupled to an apparatus holder;
receiving at least a portion of the laser radiation from the first laser light source at a first convex mirror of a first optical light guide via a first opening in a first hollow mirror of the first optical light guide, the first optical light guide being a component of the first assembly;

deflecting the portion of the laser radiation from the first convex mirror to a first concave mirror surface of the first hollow mirror;

deflecting the portion of the laser radiation from the first concave mirror surface of the first hollow mirror directly through a first light outlet opening of the first assembly to a first focal point associated with the first assembly;

adjusting a distance between a component surface and the first focal point with respect to a first area of the target structure;

receiving at least a portion of the laser radiation from the second laser light source at a second convex mirror of a second optical light guide via a second opening in a second hollow mirror of the second optical light guide, the second optical light guide being a component of the second assembly;

deflecting the portion of the laser radiation from the second convex mirror to a second concave mirror surface of the second hollow mirror;

deflecting the portion of the laser radiation from the second concave mirror surface of the second hollow mirror directly towards and through a second light outlet opening of the second assembly to a second focal point associated with the second assembly; and adjusting a distance between a component surface and the second focal point with respect to a second area of the target structure, the first area of the target structure being a different depth within tissue from the second area of the target structure;

wherein the laser radiation from each of the sources has a lower intensity in a center of a beam of the laser radiation than in an edge region of the beam of the laser radiation.

18. The method of claim 17, further comprising:

at least intermittently transmitting a control signal from a control unit to at least one of the first laser light source, the second laser light source, the first optical light guide, the second optical light guide, the first adjustment element and the second adjustment element.

19. The method of claim 17 further comprising:

issuing a first control signal from a control unit to the first adjustment element of the first assembly to adjust a distance between the surface of the skin and the first focal point associated with the first assembly to position the first focal point with respect to a first area of the target structure, and issuing a second control signal from the control unit to the second adjustment element of the second assembly to adjust a distance between the surface of the skin and the second focal point associated with the second assembly to position the second focal point with respect to a second area of the target structure, the first area of the target structure being different from the second area of the target structure.

* * * * *